United States Patent
Janicki et al.

(10) Patent No.: US 12,303,280 B2
(45) Date of Patent: May 20, 2025

(54) METHOD FOR DETERMINING ELECTRICAL ACTIVITY OF CARDIAC MUSCLE

(71) Applicant: PRIMAX MEDICA SP. Z O.O., Puszczykowo (PL)

(72) Inventors: Jerzy Stanislaw Janicki, Puszczykowo (PL); Lukasz Jerzy Janicki, Puszczykowo (PL)

(73) Assignee: PRIMAX MEDICA SP. Z O.O., Puszczykowo (PL)

( * ) Notice: Subject to any disclaimer, the term of this patent is extended or adjusted under 35 U.S.C. 154(b) by 957 days.

(21) Appl. No.: 17/426,199

(22) PCT Filed: Jan. 28, 2020

(86) PCT No.: PCT/IB2020/050639
§ 371 (c)(1),
(2) Date: Jul. 28, 2021

(87) PCT Pub. No.: WO2020/157642
PCT Pub. Date: Aug. 6, 2020

(65) Prior Publication Data
US 2022/0175301 A1 Jun. 9, 2022

(30) Foreign Application Priority Data
Jan. 28, 2019 (EP) ..................... 19461508

(51) Int. Cl.
*A61B 5/366* (2021.01)
*A61B 5/30* (2021.01)
*A61B 5/358* (2021.01)
*A61B 5/36* (2021.01)

(52) U.S. Cl.
CPC ............... *A61B 5/366* (2021.01); *A61B 5/30* (2021.01); *A61B 5/358* (2021.01); *A61B 5/36* (2021.01)

(58) Field of Classification Search
CPC ........... A61B 5/366; A61B 5/358; A61B 5/30; A61B 5/36
See application file for complete search history.

(56) References Cited

U.S. PATENT DOCUMENTS

2004/0111021 A1* 6/2004 Olson .................... A61B 5/341
  600/407
2015/0011862 A1 1/2015 Chaykovskyy

OTHER PUBLICATIONS

Franz M.R., Bargheer K. et al., "Monophasic action potential mapping in human subjects with normal electrocardiogram: direct evidence for the genesis of T wave.", Circulation, 75 (1987) 379.
(Continued)

*Primary Examiner* — Jonathan T Kuo
(74) *Attorney, Agent, or Firm* — Dickinson Wright PLLC; Andrew D. Dorisio

(57) ABSTRACT

The object of the invention is a method for determining electrical activity of cardiac muscle, characterised in that the resultant electric potential ($V_{wyp}$) forming the QRS complex in the electrocardiogram obtained during the ECG test is decomposed into partial potentials corresponding to the depolarization of specific areas (i) of the left ventricular muscle (MS).

6 Claims, 11 Drawing Sheets

(56) References Cited

OTHER PUBLICATIONS

Figure 1:
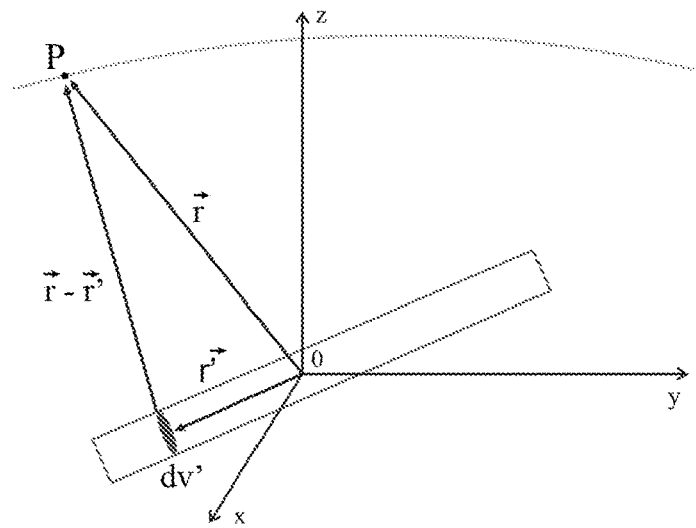

Litovsky S.H., Antzelevitch C., "Rate dependence of action potential duration and refractoriness in ventricular endocardium differs from that of epicardium: role of the transient outward current.", J. Am. Coll. Cardiel., 14 (1989) 1053.
Malmivuo J., Plonsey R., "Bioelectromagnetism", New York and Oxford, Oxford University Press, 1995. Bers D. M. "Excitation-contraction coupling and cardiac contractile force", 2nd ed., Dordrecht-Boston-London, Kulwier Academic Publishers, 2001.
Rubart M., Zipes D., "Heart disease: a textbook of cardiovascular medicine" chapter in: "Genesis of cardiac arrythmias: electrophysiological considerations", Philadelphia, W. B. Saunders Co., 2001.
Levkov L. C. "Orthogonal electrocardiogram derived from the limb and chest electrodes of the conventional 12-lead system", Med. Biol. Eng. Com put. 25 (1987) 155.
Dqbrowska B., Dqbrowski A. Handbook of electrocardiography, for medical students and professionals, in Polish, original title "Podr(;cznik elektrokardiografii," 1999, 4th edition.
W . . . staw T., "Normogram for determination of the electric axis of the cardiac muscle", in Polish, original title "Normogram do okreslania osi elektrycznej serca," Kardiologia Polska, Kardiol. Pol., 6 (1963) 113.
Le Grice I. J., Hunter P. J., Smaill B.H., "Laminar structure of the heart: A mathematical model," Am. J. Physiol., 272 (1997) H2466-H2476.
Clayton R. H., Parkinson K., Holden A. V., "Re-entry in computational models of ischaemic myocardium", Chaos, Solitons and Fractals, 13 (2002) 1671-1683.

Drouin E, Charprentier EF. et al., "Electrophysiologic characteristics of cells spanning the left ventricular wall of human: evidence for presence of M cells," J. Amer. Coll. Cardiel., 26 (1995) 185.
Litovsky S. H., Antzelevitch C., "A subpopulation of cells with unique electrophysiological properties in the deep subendocardium of the canine ventricle. The M cell", Circ. Res., 68 (1991) 1729.
Antzelevitch C., Sicouri S., Lucas A. et al., "Regional differences in the electrophysiology of ventricular cells: physiological and clinical implications" in "Cardiac electrophysiology: from cell to bedside", Eds. Zipes D.P., Jalife J., Saunders W. B., Comp., Philadelphia, 1995, p. 228.
Daubechies I., "The wavelet transform, time-frequency localizations and signal analysis" IEEE Transaction on Inform. Theory, 35(5) (1990) 961-1005.
Sahambi J. S., Tandon S.N., Blatt R. K. P., "Using wavelet transform for ECG characterization", IEEE EMB Magazine, Jan./Feb. 1997,, pp. 77-83.
Hormac C., Vetterli M., "Orthogonal time-varying filter banks and wavelet packets", IEEE Transaction on Signal Processing, 10(42) (1994) 2650-2663.
Vetterli M.,"Wavelets and filter banks" IEEE Transaction on Signal Processing,9 (40) (1992) 2207-2232.
J S Janicki et al.; Application of SFHAM Model for Diagnosis of Ischemic Heart Disease 1; Electrocardiology 2014—Proceedings of the 41st International Congress on Electrocardiology; Jun. 2014.
Janicki; Partial potentials of selected cardiac muscle regions and heart activity model based on single fibres; Medical Engineering Physics, Butterworth-Heinemann, Great Britain; Dec. 2009.

\* cited by examiner a) $r_o=20(-\cdot-), 30(\cdots), 40(—); \quad \beta=0$  b) $r_o=20(-\cdot-), \; 30(\cdots), \; 40(—);$ $\beta=-31°$

Fig. 13 (a, b)

a) $r_o=40; \; \beta=-57°(-\cdot-), \; 0°(\cdots), \; 57°(—)$  b) $r_o=40; \; \beta=-31°; \; A_1(-\cdot-), 2A_1(\cdots), 4A_1(—)$ a) (WMN)    b) ( MN)

c) (W N)    d) (WM )

a)    b)

X          Y          Z

X          Y          Z

X  (V(+)/V(-) = 21/13)   Y  (V(+)/V(-) = 61/25)   Z  (V(+)/V(-) = 46/12)

X  (V(+)/V(-) = 44/13)   Y  (V(+)/V(-) = 48/25)   Z  (V(+)/V(-) = 36/12)

METHOD FOR DETERMINING ELECTRICAL ACTIVITY OF CARDIAC MUSCLE

The invention relates to a method for determining electrical activity of cardiac muscle based on a bioelectrical signal acquired from the surface of the chest, in particular based on the electric potential forming the QRS complex in an electrocardiogram.

The assessment of the heart bioelectrical signal with the resting ECG is the simplest and the cheapest method enabling the detection of many heart diseases including arrhythmia, myocardial ischemia, and myocardial infarction. However, its diagnostic efficiency is highly unsatisfactory. Increasing the efficiency of the analysis of the heart bioelectrical signal in this context requires going beyond the scope of the previously used assessment of this signal.

The purpose of the invention is then to provide a new method for analysing the QRS complex.

To achieve it, the SFHAM model [1] of electrical heart activity is used, describing the mechanism of QRS complex formation in a way that allows for a detailed reproduction of the depolarization changes in individual areas of the myocardium. The practical implementation of the model is carried out through analysis of standard electrocardiograms, which results in the calculation of the electrical activity parameters of at least five areas of the heart, in particular the left ventricle.

The idea of this method was disclosed in publications [1] and [21], however, none of these publications disclose the method of determining the parameters of mathematical functions describing changes in the value of partial potentials, in particular the positions of extremes of these functions.

SUMMARY OF THE INVENTION

The object of the invention is a computer-implemented method for determining the electrical activity of the cardiac muscle, wherein the resultant electric potential ($V_{wyp}$) forming the QRS complex in the standard electrocardiogram is decomposed into partial potentials corresponding to the depolarization of specific areas (i) of the left ventricular muscle (CM).

Preferably, each partial potential corresponds to the following areas (i): the interventricular septum (PR) as well as the anterior wall (P), inferior wall (ŚD), lateral wall (ŚB), and posterior wall (ŚT), respectively.

The decomposition is carried out in such a way that, on the basis of the theoretical SFHAM model of electrical heart activity, mathematical functions describing changes in the partial potential values are determined, and then their parameters are selected so that the superposition of the values of these functions is as close as possible to the resultant potential ($V_{wyp}$) measured during the ECG test.

Each of the partial potentials is determined by two functions: $V_{1,i}(t)$ and $V_{2,i}(t)$, corresponding to the depolarization of a specific area of the left ventricular muscle, where "i" denotes the specific area of the left ventricular muscle, in particular i={PR, ŚP, ŚD, ŚB, ŚT}.

Each of these functions has negative or positive values and one extremum, wherein the beginning of the emergence of these potentials ($t_{0(1),i}$ and $t_{0(2),i}$) and their end ($t_{k(1),i}$ and $t_{k(2),i}$) is considered the time at which the potential value is greater than its arbitrarily set minimum value, and the sum of the values of these potentials determines the electrical activity of the specific area of the left ventricular muscle.

The order of occurrence of the extrema of above mentioned functions is determined from a the SFHAM model and the positions of extrema are determined by:

- making a series of transformations of the potential values for (X Y Z) coordinates in the orthogonal system, consisting in rotation of the coordinates in the range (0÷90)° with respect to two selected axes by (α,β) angles,
- calculating, for each rotation angle, the extremal values of the partial potentials for each of the (XYZ) coordinates, by using deconvolution and convolution, and a low-pass filter with parameters corresponding to the function describing the partial potentials, and then
- selecting the angles for which the differences in the positions of extrema for each of the partial potentials in the XYZ system, respectively, are the smallest.

Preferably, the analysis of the resultant potentials (QRS complexes) for each lead is made on the basis of averaged values, transformed into the orthogonal Frank lead system, whose origin is located in the center of the heart, the X axis directed towards the patient's left hand, the Y axis towards his feet and the Z axis pointing to the patient's back.

Preferably, having determined the parameters of the functions $V_{1,i}(t)$ and $V_{2,i}(t)$, describing the waveforms of the partial potentials, the area under the curve of each of these potentials for X, Y, Z coordinates is calculated, in particular using the formulae:

$$A_{1,i} = \sum_{j=\{x,y,z\}} \int_{t_{0(1),i}}^{t_{k(1),i}} |V_{1,i,j}| dt$$

$$A_{2,i} = \sum_{j=\{x,y,z\}} \int_{t_{0(2),i}}^{t_{k(2),i}} |V_{2,i,j}| dt$$

where $t_{0(1),i}$ and $t_{0(2),i}$ denote the time the potential begins to appear, and $t_{k(1),i}$ and $t_{k(2),i}$ the time it ends to appear for each of the individual areas, respectively.

Then, preferably:

The parameter describing the resultant electrical activity of the ventricles is calculated:

$$A_{wyp} = \sum_{j=\{x,y,z\}} \int_{t_0}^{t_{end}} |V_{wyp}| dt \qquad (29)$$

The normalised partial potentials ($U_{1,i}$, $U_{2,i}$ and $U_{wyp}$) are calculated as follows:

$$U_{1,i} = \frac{A_{1,i} N_{wyp}}{N_{1,i} A_{wyp}} \cdot 100\%;$$

$$U_{2,i} = \frac{A_{2,i} N_{wyp}}{N_{2,i} A_{wyp}} \cdot 100\%;$$

$$U_{wyp} = \frac{A_{wyp}}{N_{wyp}} \cdot 100\%$$

wherein ($N_{1,i}$, $N_{2,i}$ oraz $N_{wyp}$) are parameters determined for the partial potentials, with normal electrical activity treated as a norm;

The parameter describing the change in electric charge distribution during the depolarization of each myocardium area is calculated:

$$J_i = \frac{U_{2,i}}{U_{1,i}}.$$

Preferably, the duration times of the partial potentials for each area of the left ventricular muscle are calculated with the relationship:

$$t_{1,i} = \sum_{j=\{x,y,z\}} \left((t_{k(1)} - t_{0(1)})_j\right)_i$$

$$t_{2,i} = \sum_{j=\{x,y,z\}} \left((t_{k(2)} - t_{0(2)})_j\right)_i$$

The object of the invention is also a device configured to implement the method according to the invention, a computer program implementing the method according to the invention, as well as a carrier comprising such a computer program.

Decomposition of the electrocardiogram into partial potentials corresponding to particular areas of the left ventricular muscle (e.g., the interventricular septum, anterior, inferior, lateral and posterior wall) and determination of the parameters related to the duration and electrical activity allow the condition of individual areas of the myocardium to be assessed and may enable early diagnostics of various pathological changes of the heart in patients for whom the results of a standard ECG test are inconclusive.

An example of the use of QRS complex decomposition in a standard ECG according to the invention is described in the publication "Janicki J S, Teresińska A, Leoński W, Chąpiński M, Sobieszczańska M, Piotrowicz R, *Application of SFHAM Model for Diagnosis of Ischemic Heart Disease 1*", Electrocardiology 2014—proceedings of the 41st International Congress on Electrocardiology, 7 Jun. 2014 (2014 Jun. 7, pages 187-190".

The invention will now be described in detail in an exemplary embodiment, with reference to a drawing in which the individual figures show:

FIG. 1. Typical CM fibre and the coordinate system fitted in the fibre centre indicated by 0. P represents the measurement point and dv' is an infinitesimally small volume.

Figure 2:
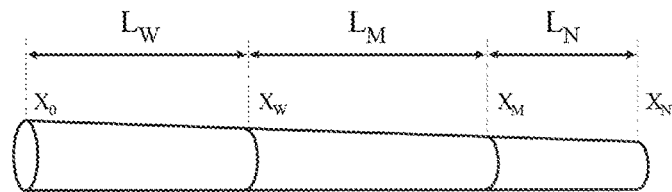

FIG. 2. Three parts of a single fibre associated with endocardial, myocardial, and epicardial cells (with $L_W$, $L_M$ and $L_N$ length, respectively).

Figure 3:
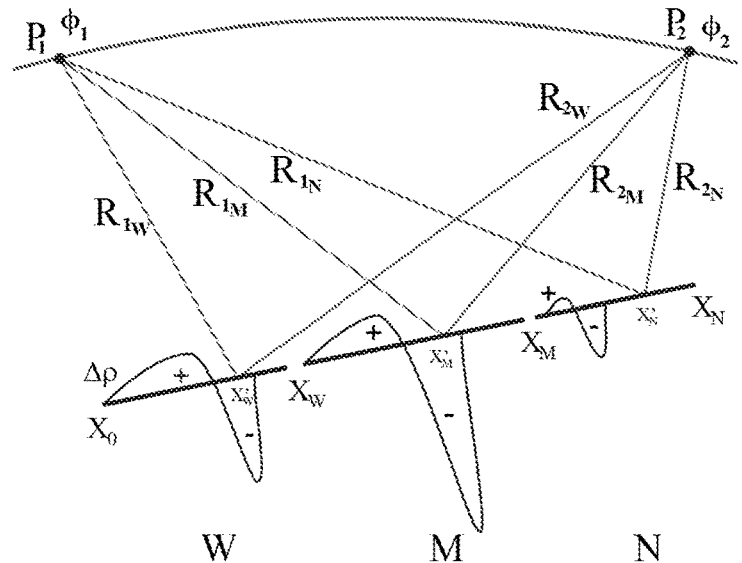

FIG. 3. Plot of the resultant charge density $\Delta\rho$ for individual parts of the MS fibre and electric potential $\phi_i$ at $P_i$ points located on the surface of the chest.

Figure 4:
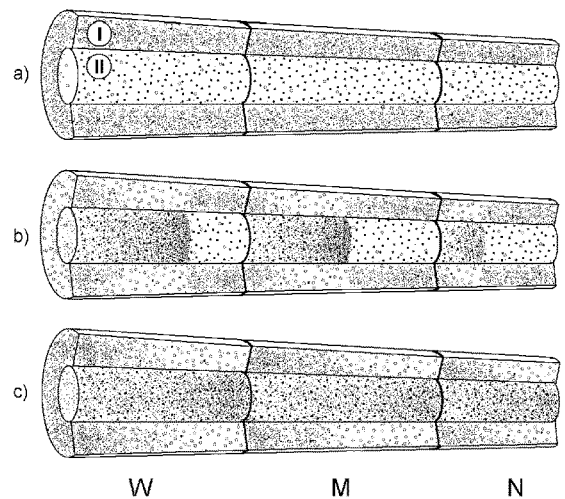

FIG. 4. Model distribution of $Na^+$(•), $K^+$(●) and $Cl^-$ (○) ions in extra- (I) and intracellular (II) areas of a three-part CM fibre (W, M, N). a) resting state of the cells; b) and c) subsequent phases of the depolarization of fibre cells.

Figure 5:
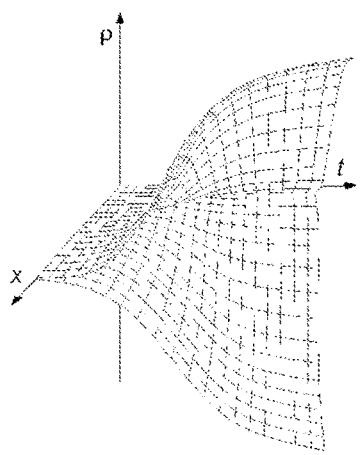

FIG. 5. Change in the electric charge density inside ($\rho_+$) and outside ($\rho_-$) in one part of the fibre (x') during the fibre depolarization (t').

Figure 6:
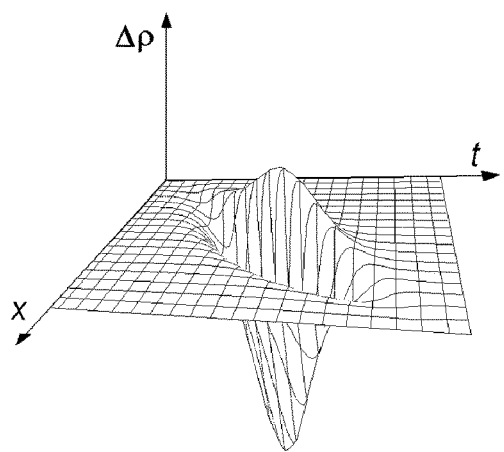

FIG. 6. Change in the resultant electric charge density $\Delta\rho$ along one part of the fibre (x') during the depolarization process (t').

Figure 7:
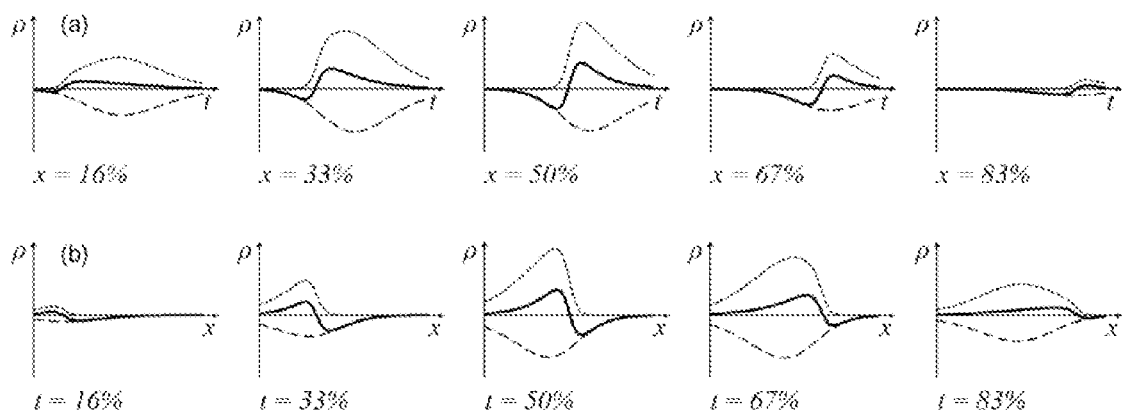

FIG. 7. Plots of typical charge densities calculated from equations (12-15) as a function of time (a) and position measured along the fibre (b). The x(a) parameter denotes the position along the fibre length expressed in percents, while t(b) is the total depolarization time expressed in percent; solid lines—total charge density $\Delta\rho$; dotted lines—positive charge density $\rho_+$; dashed lines—negative charge densities $\rho$.

Figure 8:
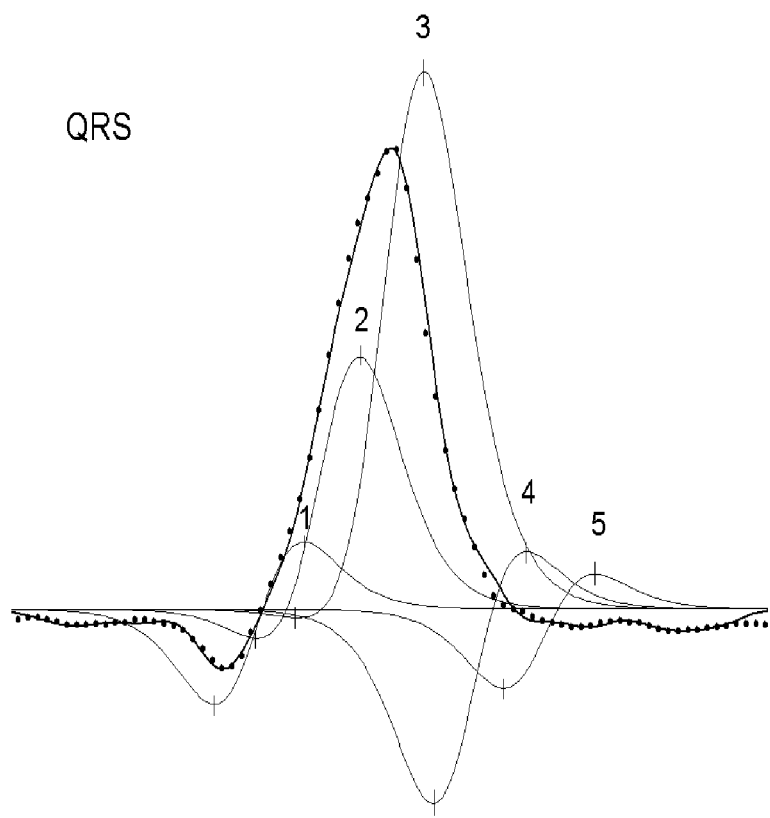

FIG. 8. Plots of negative/positive potentials appearing during the cardiac muscle depolarization. Time-dependencies of the total (-), experimental (•), and transient (-) potentials originated from individual bundles.

Figure 9:
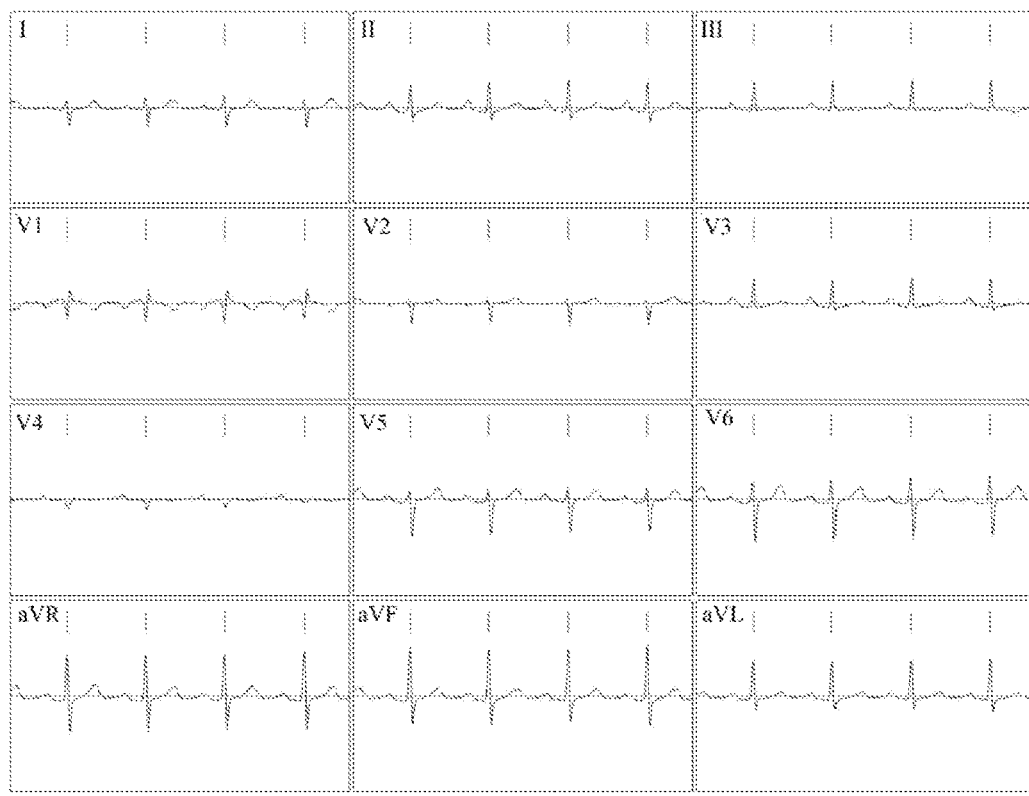

FIG. 9. Electrocardiogram for 12 leads with indicated centre points.

Figure 10:
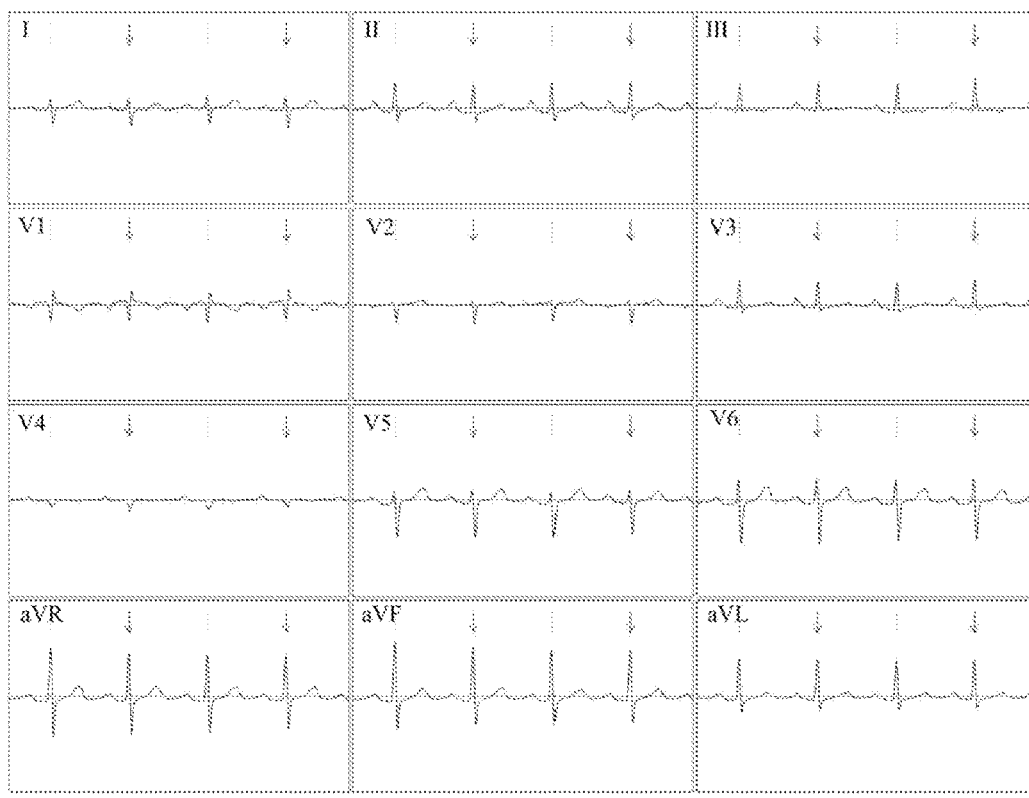

FIG. 10. QRS complexes selected for averaging indicated with arrows.

Figure 11:
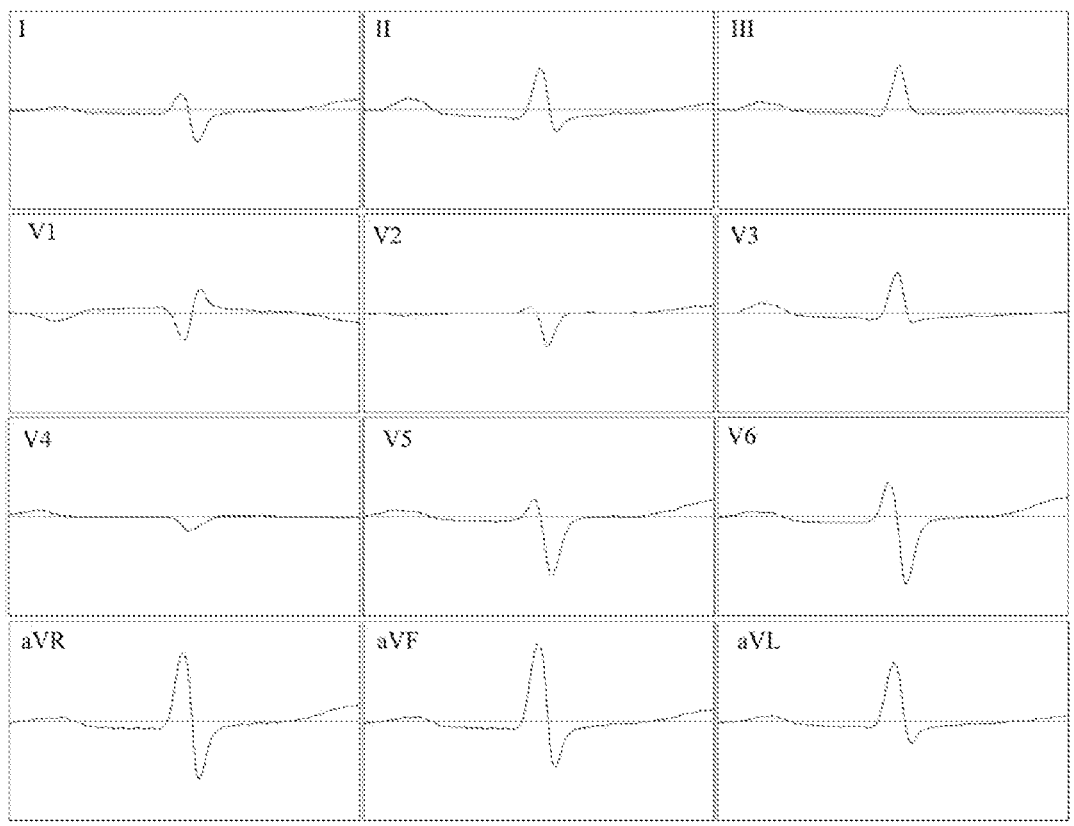

FIG. 11. Averaged values of the QRS complex potential for each of the 12 leads.

Figure 12:
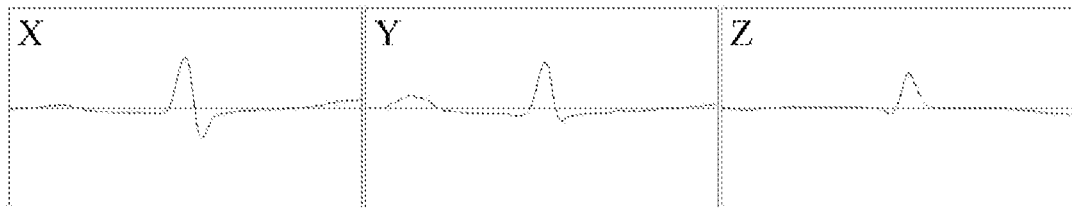

FIG. 12. (X, Y, Z) components of the resultant potential in the orthogonal coordinate system.

Figure 13:
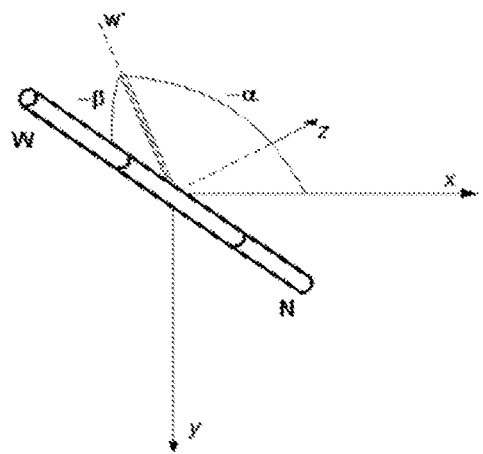

FIG. 13 (*c*) Position of the cardiac muscle bundle (including its endocardium (W) and epicardium (N)) in the (xyz) orthogonal coordinate system associated with the patient's body. The origin of the coordinate system is located in the center of the heart, the X axis directed towards the patient's left hand, the Y axis towards his feet, and the Z axis pointing to the patient's back.

FIGS. 13 (*a*), (*b*). Distribution of the potential $\varphi(x)$ for three different distances between the geometric centre of the bundle and the (XY) plane for $A_1$=const. and the angles: b) $\beta$=0°, and c) $\beta$=−31°. The vertical signs indicate the extreme $\varphi(x)$ values.

Figure 14:
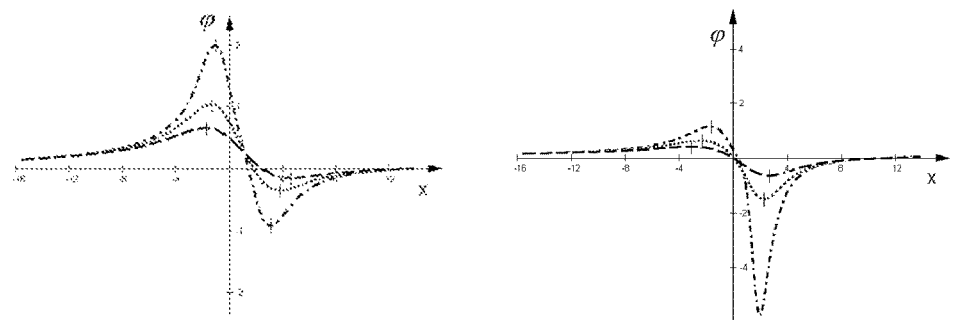
Figure 14:
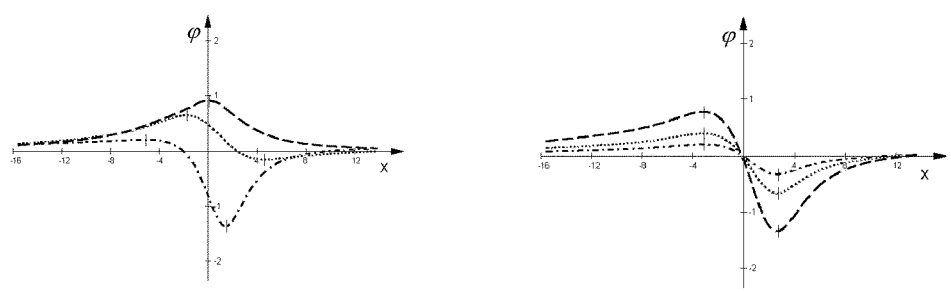

FIG. 14. Distribution of $\varphi(x)$ potential: a) for $r_0$=40 and $A_1$=const. and three different angles ($\beta$), b) for $r_0$=40 and $\beta$=−31° and three different amplitude values $A_1$. The vertical signs indicate the extreme $\varphi(x)$ values.

Figure 15:
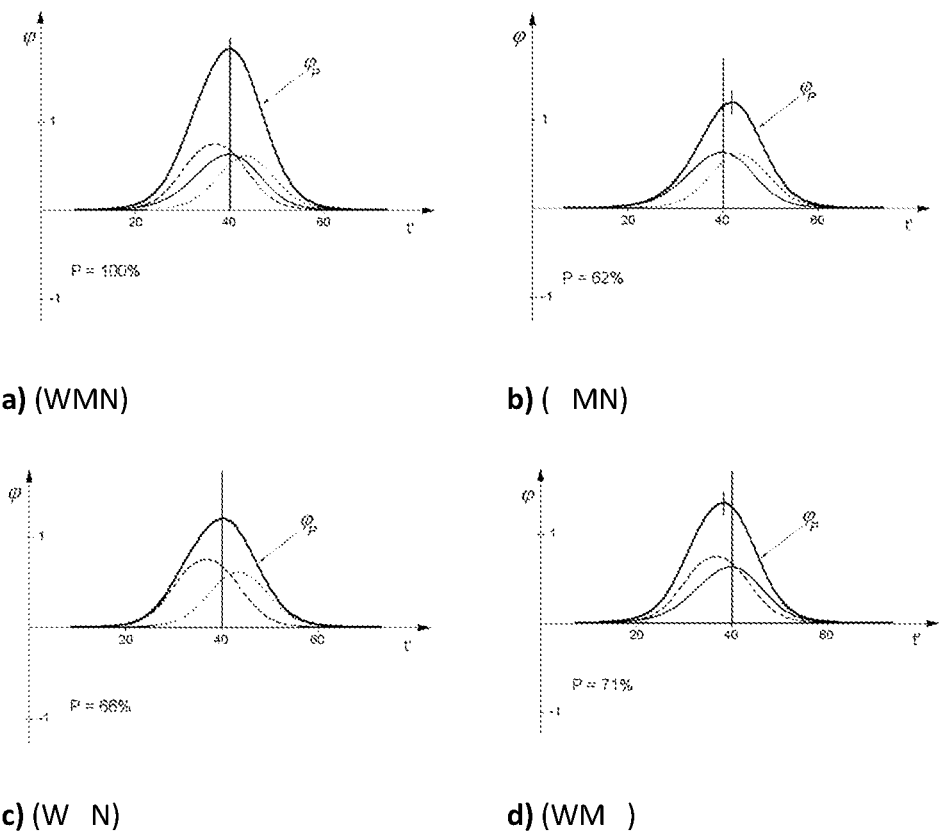

FIG. 15. Time dependence of the resultant potential, $\varphi_P$, of the CM bundle obtained while taking into account: a) the subendocardial part W (---), the part associated with the M cells (-), and the subepicardial part N (•••), b) the (M, N) parts, c) the (W, N) parts, d) the (W, M) parts. P—is the percent of the area under each instantaneous potential curve relative to the one of FIG. 14 (*a*) that was assumed as 100%.

Figure 16:
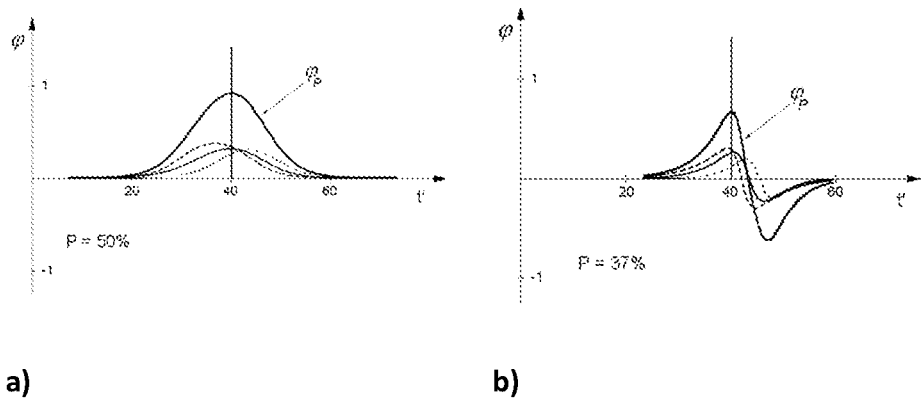

FIG. 16. Time dependence of the $\varphi_P$ potential appearing during the depolarization of the three parts of a CM bundle: a) with amplitude ½ A, and b) with a very high rate of the charge propagation in the area II.

Figure 17:
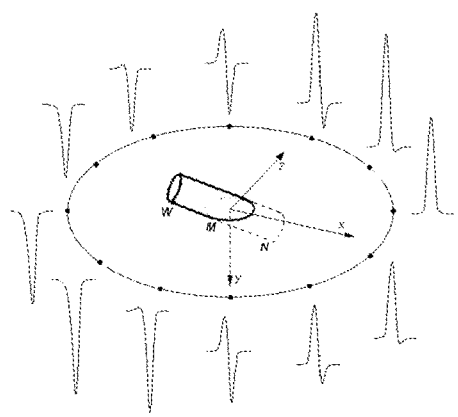

FIG. 17. Time dependence of the partial potential for a single bundle, calculated at sites equidistant from its centre.

Figure 18:
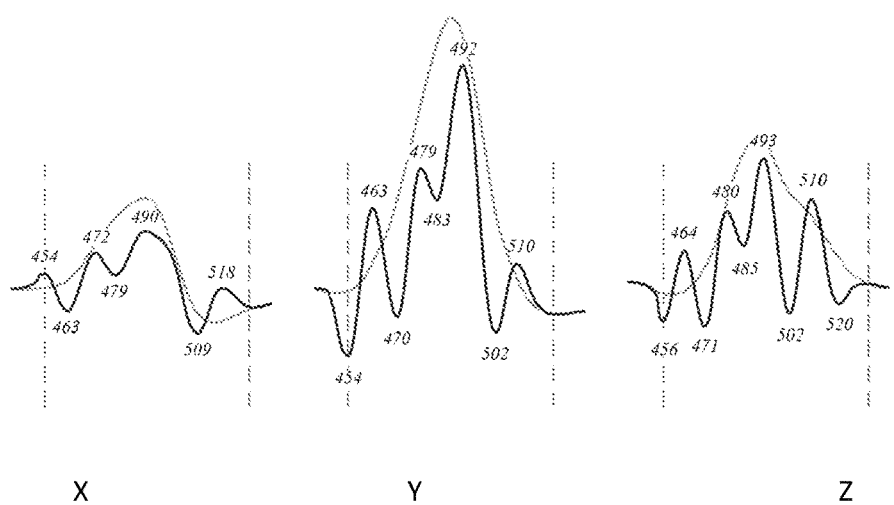

FIG. 18. Positions of extreme values of partial potentials in the orthogonal coordinate system (XYZ) with no optimization of rotation angles.

Figure 19:
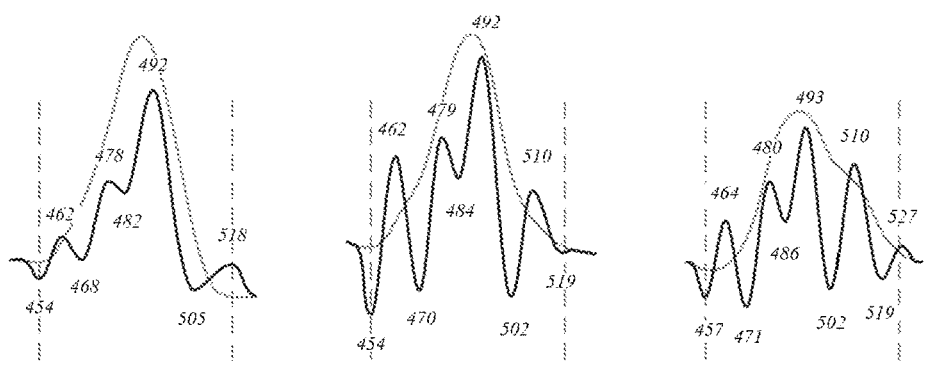

FIG. 19. Positions of extreme values of the partial potentials in the (XYZ) orthogonal coordinate system after optimization of the rotation angles.

Figure 20:
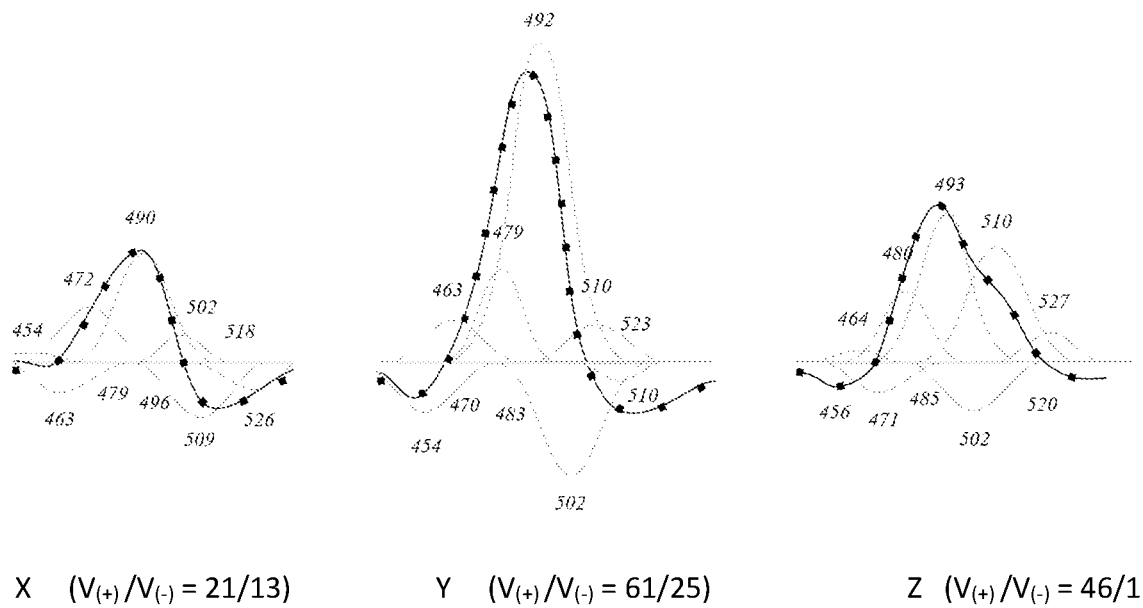

FIG. 20. Partial potential waveforms without rotation. The ratio of the sum of positive potentials to negative potentials for (XYZ) is given in parentheses.

Figure 21:
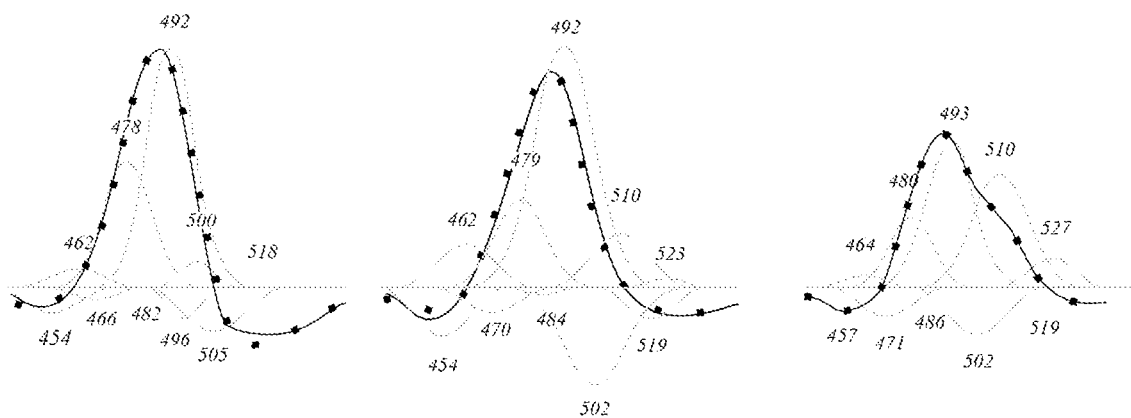

FIG. 21. Partial potential waveforms for optimally selected rotation angles. The ratio of the sum of positive potentials to negative potentials for (XYZ) is given in parentheses.

Figure 22:
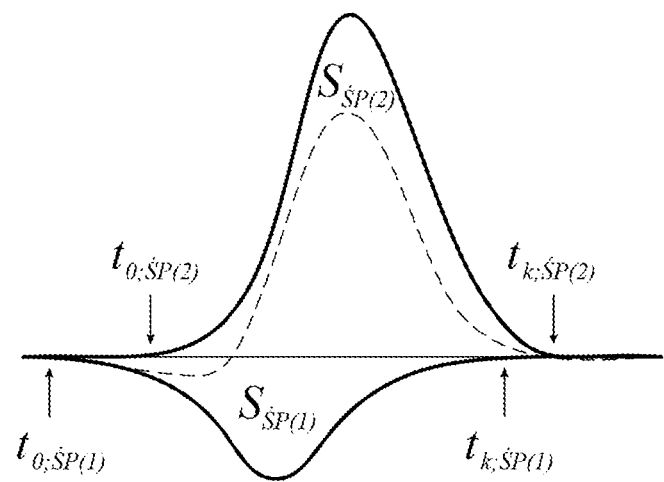

FIG. 22. Typical potential waveform for the anterior wall along the Y axis. The sum of these potentials indicated as (---) is a negative/positive potential.

Figure 23:
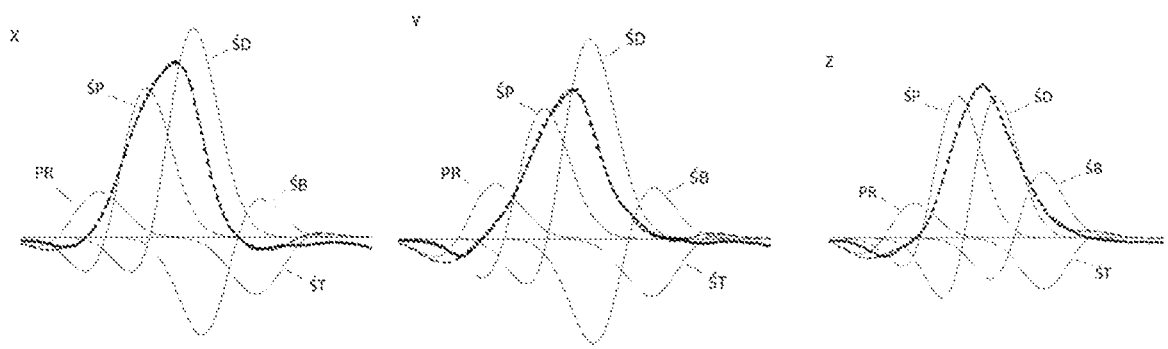

FIG. 23. QRS signals (dots) in the orthogonal Frank lead system and their numerical equivalents calculated from the model. Total potential—dashed thick line; negative/positive partial potentials—thin solid line. PR, ŚP, ŚD, ŚB, and ŚT correspond to the interventricular septum, and the anterior, inferior, lateral, and posterior walls, respectively.

Figure 24:
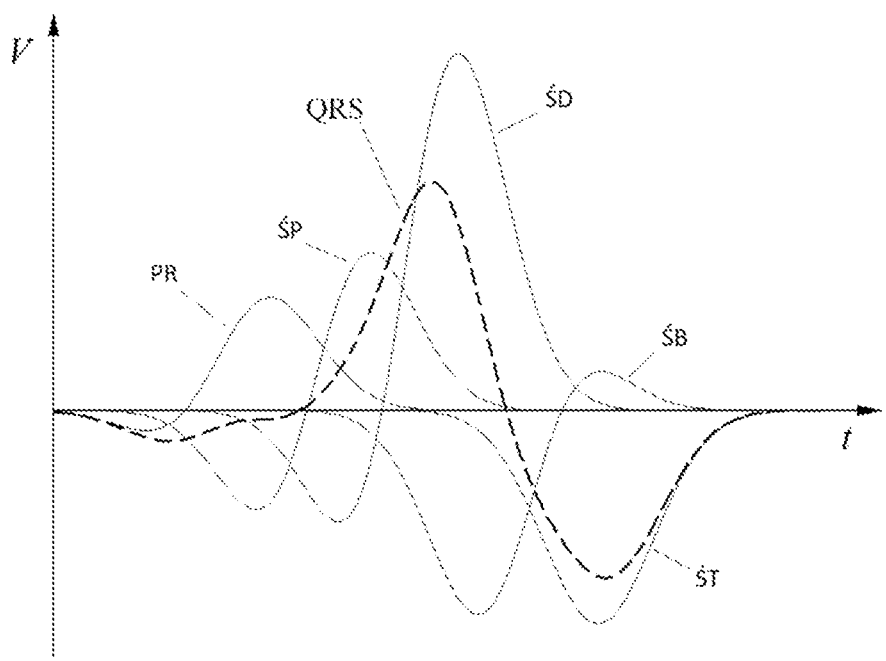

FIG. 24. Time dependence of the negative/positive partial potentials forming the QRS complex, appearing as a result of the depolarization of the corresponding areas of the left ventricular muscle: interventricular septum (PR), and anterior (ŚP), inferior (ŚD), lateral (ŚB), and posterior (ŚT) walls.

Figure 25:
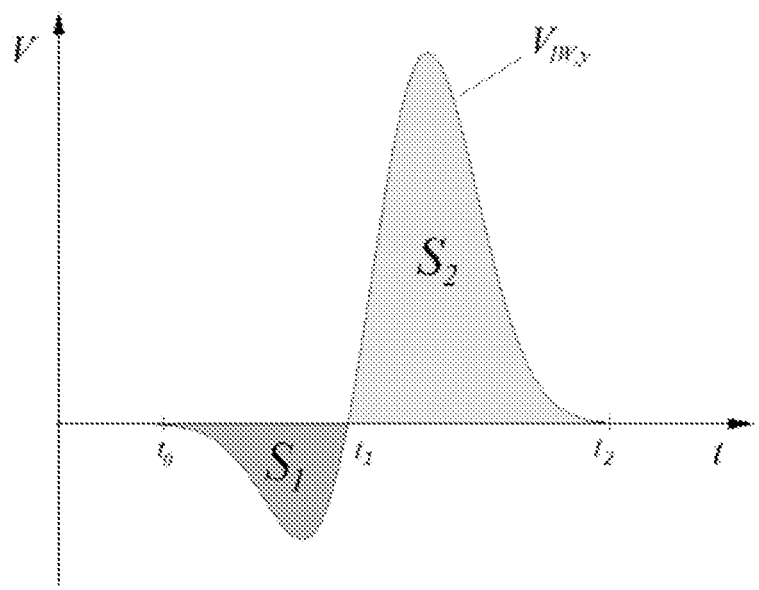

FIG. 25. Typical waveform of the negative/positive partial potential appearing during depolarization of the inferior wall, which has negative (1) and positive (2) values. The surfaces comprising each of the areas are marked.

SFHAM MODEL (SINGLE FIBRE BASED HEART ACTIVITY MODEL)

The electrocardiogram illustrates the time course of the electric potentials measured at certain points on the surface of the chest. The value of these potentials is the sum of all potentials originating from the distribution of charges associated with their flow along the fibres located in the myocardium. In the proposed model, the charges move along a single fibre located in the cardiac muscle and the emerging potential can be described using the well-known relationship:

$$\Phi(\vec{r},t) = \int \frac{\Delta\rho(\vec{r}',t)}{|\vec{r}-\vec{r}'|}dv' \qquad (1)$$

where $\Delta\rho(\vec{r}',t)$ is the effective charge density (associated with the distribution of cations and anions), $dv'$ is an infinitesimally small volume element, and the integration is carried out along the entire fibre length. The location of the volume element and the measurement point are determined by the vectors $\vec{r}'$ and $\vec{r}$, respectively. These vectors are defined at a given point P in the coordinate system located at the centre of a single fibre, as shown in FIG. 1.

It should be borne in mind that the properties of the fibre change along its length, as reported in ref. [2,3]. We divided the fibre into three parts marked by W, M and N, and identified as subendocardial (W), myocardial (M), and subepicardial (N) parts with lengths LW, LM, and LN, respectively (FIG. 2).

In the further part of the analysis of this issue, it will be more convenient to express the boundary points using $x_0$, $x_W$, $x_M$, $x_N$ coordinates.

Assuming that t' is the time interval in which the depolarization wave passes the entire fibre, and $x'_j$ is contained in the interval $\langle -L_j/2, L_j/2 \rangle$ for $j \in \{W, M, N\}$, the density for the whole fibre can be expressed by the ($\rho_W$, $\rho_M$, $\rho_N$) quantities corresponding to its individual parts:

$$\rho_\pm(x',t') = \begin{cases} \rho_W(x'_W, t'_W) dla x'_0 \leq x' \leq x'_W \\ \rho_M(x'_M, t'_M) dla x'_0 \leq x' \leq x'_M \\ \rho_N(x'_N, t'_N) dla x'_0 \leq x' \leq x'_N \end{cases} \qquad (2)$$

For a given time moment, these parts are characterized by charge densities with different values and distributions. In addition, if we take into account different points on the patient's body ($P_1$ and $P_2$)—as shown in FIG. 3—the potential values ($\phi_1$ and $\phi_2$) depend on the resultant charge density in individual parts (WMN) and the distances ($R_{iW}$, $R_{iM}$, $R_{iN}$) between the $P_i$ points, where i=(1, 2), and the corresponding parts of the fibre.

It follows from the formula (1) that a proper determination of the function describing the dependence of electric potential as a function of time and position in space is strongly related to the distribution of charge density. Thus, the resultant electric charge during the depolarization appears together with the change of parameters of the emerging charge density waves (amplitude, mutual time shift), where also the electrical parameters of the area of the cardiac muscle of interest to us are changing. Both the total charge detected in a given area and the moments of different orders—including the electric dipole moment, can change. The total electric charge generated during the depolarization of a given fibre is related to the density distribution of positive ($\rho_+$) and negative ($\rho_-$) charges by the following relationship:

$$q(t')=\int_F(\rho_+(\vec{r}',t')+\rho_-(\vec{r}',t'))d\vec{r}' \qquad (3)$$

where the integration is carried out over the entire fibre area F, and the $\vec{r}'$ vector defines the position of a given fragment in a given coordinate system.

The waves of negative and positive charge travelling in the same direction have a similar character, the key issue is, however, the mutual relationship between them. Of importance here are parameters such as the amplitude values of these waves, the mutual position, and the velocity of propagation of the perturbation along the fibre. In a special case, when the amplitudes of both waves are simultaneously identical and their mutual shift is equal to zero, both waves cancel out giving no contribution to the measured ECG signal. In addition, the final result may also be slightly affected by the dipole moment appearing in the myocardium fibres, wherein the dipole moment vector $\vec{p}$ is determined by formula (4):

$$\vec{p}(t')=\int_F \vec{r}'(\rho_+(\vec{r}',t')-\rho_-(\vec{r}',t'))d\vec{r}' \qquad (4)$$

It is assumed that the effect of the higher moments contribution in the distribution of the measured potential is negligibly small. Taking into account the geometry of a single fibre, it is assumed that we are dealing here with a one-dimensional charge distribution and, as a result, the fibre under consideration is treated as a one-dimensional system. Then, in the integrals appearing in formulae (3) and (4), the $\vec{r}'$ vector is replaced by the x' coordinate. This operation allows the calculations to be significantly simplified. Then, the dependence of the value of the emerged electric charge and the dipole moment on time is described by equations (5) and (6), respectively. The equations account for the density changes resulting from the spread of charge, and this in one part of the fibre only.

$$q(t') = \frac{A_+}{k_{t'}}\sum_{j=1,2}(-1)^j\left[k_{x'}k_{t'}\ln\left(e^{\frac{x'_j k_{t'}+k_{x'}(t'+dt')}{k_{x'}k_{t'}}}+1\right)+ \right.$$

$$x'_j k_{t'} + k_{x'}(t'+dt')\Big] -$$

$$\frac{A_-}{k_{t'}}\sum_{j=1,2}(-1)^j\left[k_{x'}k_{t'}\ln\left(e^{\frac{x'_j k_{t'}+k_{x'}(t'+dt')}{k_{x'}k_{t'}}}+1\right)+ \right.$$

$$\left. x'_j k_{t'} + k_{x'}(t'+dt')\right] \qquad (5)$$

-continued then $$p(t') = A_+ \frac{k_{x'}}{k_{t'}} \sum_{j=1,2} (-1)^j \left[ k_{x'} k_j dilog\left(e^{-\frac{x'_j k_t + k_x(t'+dt')}{k_x k_t}} + 1\right) + \right.$$
$$x'_j k_{t'} \ln\left(e^{-\frac{x'_j k_t + k_x(t'+dt')}{k_x k_t}} + 1\right) \right] -$$
$$A_- \frac{k_{x'}}{k_{t'}} \sum_{j=1,2} \left[ k_{x'} k_{t'} dilog\left(e^{-\frac{x'_j k_t + k_x(t'+dt')}{k_x k_t}} + 1\right) - \right.$$
$$\left. x'_j k_{t'} \ln\left(e^{-\frac{x'_j k_t + k_x t'}{k_x k_t}} + e^{\frac{dt'}{k_t}}\right) + x'_j dt' \right]$$
(6)

The above formulae contain a special function dilog (x'), which is defined as follows:

$$dilog(x') = \int_1^{x'} \frac{\ln(\tau)}{1-\tau} d\tau \quad (7)$$

Due to the difficulties in finding a fully analytical expression for the charge and the dipole moment appearing here, the issue was solved by numerical integration. The dynamics of the charge density distribution are reflected in the electric potential, as measured on the surface of the body, emerging during the electrical activity of the heart, the value of which at a given measurement point depends, inter alia, on the magnitude of the resultant electric charge existing at a given time. The contribution to the electric potential originating from a single charge is isotropic. Meanwhile, the potential measured in practice is anisotropic. In different parts of the analyzed fibre section, the processes start at different time moments, and at different angles to the surface of the body, so that the resultant charge associated with different areas has a more complex spatial distribution, which leads to anisotropy in its distribution. This potential is defined by the relationship (8), $$\varphi(\vec{r}, t) = \int \frac{\rho_+(\vec{r}', t') + \rho_-(\vec{r}', t')}{|\vec{r} - \vec{r}'|} dv' \quad (8)$$

between the predetermined values of the density of charge $\rho_+$ contained in the infinitesimally small volume element $dv'$, whose position relative to the geometrical centre of the fibre is described by the vector $\vec{r}'$ in the manner shown in FIG. 1. The length of this vector determines the distance of the volume element $dv'$, and the vector $\vec{r}$—the position of the measurement point from the origin of the so oriented coordinate system. The introduction of the multipole expansion into the analysis significantly simplifies the expression describing the potential of the electric field, which assumes the following form:

$$\varphi(\vec{r}, t') = \frac{q(t')}{r} + \frac{\vec{p}(t') \cdot \vec{r}}{r^3} \quad (9)$$

where q denotes the total charge in the area of cardiac muscle of interest, and $\vec{p}$ is the dipole moment. Due to different effect of the distance (r) on the value of individual terms of this equation, it is assumed that the main contribution to the potential is made by the resultant electric charge which was generated at a given time of stimulation of the fibre cells. In addition, it is taken into account that the fibre in question is composed of three parts (W, M, N), each of them being a source of an independent potential. Considering the mutual relationships between them, one can calculate the potential value at any point P, at each time during the process of cell stimulation in the whole fibre. A general method of solving this problem is shown graphically in FIG. 3, where the waveforms of the resultant charge density $\Delta\rho(x, t_k)$ calculated at a given time $(t_i)$ are presented for each part of the fibre. Thus, the potential at any point P is calculated by summing all the contributions originating from the resultant charge density that was generated along the entire fibre at a given time $(t_i)$. The potential $\varphi$ calculated in this way originates from a single fibre only, so to account for the effect of the remaining fibres forming a given bundle, the position of each fibre in relation to the geometric centre of the bundle, which is taken as the origin of the coordinate system, should be taken into account. Assuming a regular shape of the bundle in the form of a cylinder, the contribution from different amount of fibres to the potential value $\varphi_w$ is taken into account by changing the amplitude in the formula for the resultant charge density. Generally, it can be written as follows:

$$\varphi_w(P, t') = \Sigma_i \varphi_i(P, t') \quad (10)$$

The source of the heart's activity are changes in the electric charge density in its working fibres located in specific areas of the cardiac muscle, along which the resultant charge wave travels. The bundles stimulated at successive time moments make independent contributions to the total charge density, giving rise to appearance of the time and position dependent electric potentials. Consequently, the multi-centre process of generating partial potentials reflects the depolarization of individual areas of the myocardium. As a result, anisotropic potential and electric field distributions appear around the heart. The electric currents occurring in this system give also rise to appearance of an anisotropic magnetic field distribution.

Under physiological conditions, there occur various mechanisms of electric current flow associated with the flow of the positive ($Na^+$, $K^+$, $Ca^{++}$) and negative ($Cl^-$) ions. The formation and movement of the resultant charge wave along a myocardial fibre is analyzed in the intra (1) and extracellular (2) regions. The myocardial fibres are composed of cylindrical cells between which a direct contact is provided through specific low resistance links called gap junctions. Usually, the rapid rate of spread of the charge wave along the fibres depends on the efficiency and number of these links, much more numerous at the ends than at the lateral edges of the fibre. In addition, common membrane fragments of adjacent cells ensure free flow of ions and small particles between successive cells, resulting in a rapid transfer of stimulation along the fibre.

In this model, the ion channels in extra- and intracellular biological membranes play an essential role in transferring the stimulation along a fibre. The intracellular membranes account for 90% of the cell membranes, and the mitochondrial ion channels play an important role in the cellular ion homeostasis. Successive activation and deactivation processes of these channels give rise to a local increase in the density of ions which take part in transporting the electric charge. The areas containing charges are not static ones, and the dynamics of charge distribution are similar to the propagation of charge waves along successively stimulated cells of a given myocardial fibre. The dynamics of this process can be observed using a computer program that allows for simulation of various ion flows during the stimulation. The potential inside the fibre measured then with respect to the external space is −90 mV, and the highest charge concentration under physiological conditions occurs at the surface of the myocardial fibre walls.

At the time when the stimulation wave from the stimulus-conduction system reaches the first cells, a rapid influx of sodium ions ($Na^+$) into their interior results in a fast increase in the value of the emerging potential. As a result of this process, a positive charge density wave travels along the fibre in the region (1), at the same time causing the negative charge density to increase in the region (2). Taking into account the mutual relationships between the individual potentials, a simulated charge density distribution for the whole fibre at three different time moments is shown in FIG. 4-$a$), $b$), and $c$). Simulations of the positive electric charge distribution in the intra (1) and extracellular (2) regions for three parts of the fibre (W, M, N) during the resting state of cells (a) and subsequent stages of the depolarization (b and c). As a result, the groups of such fibres are treated as a sort of linear conducting systems, through which flow currents associated with ion transport processes.

The ion channels inside the cells active at that time allow for free flow of charge inside the fibre. In each case, the marked points indicate the positive charge that is inside the fibre or moves towards the fibre. In order to fully analyse this process, the differences in the distribution of potentials arising in particular parts of the myocardial wall are taken into account.

In this model, when the cells are stimulated, the density of the positive ($\rho_+$) and the negative charge ($\rho_-$) change in the intra and extracellular regions, respectively. The effective density $\rho_{\pm eff}$ is related to the amount of charge that occurs inside the volume element dv' at time t and (t−$t_0$):

$$\rho_{\pm eff} \rho_{t\pm} + \rho_{(t-t_0)\pm} \qquad (11)$$

It is therefore necessary to take into account the delay determined by the time $t_0$, because the charge density is related not only to the moving front of the charge wave at time t, but also to the conductivity of a given part of the fibre (due to this conductivity the charge density given for an earlier time affects the total density determined at a later time, which we are interested in). It should be emphasized that the delay also affects the value of the emerging potential and therefore plays a crucial role in our model. If disregarded, the densities of the positive and negative charges cancel each other leading to a zero value of the total charge density. Therefore, in future considerations, we focus on the delayed part of the charge density, as it gives a non-zero contribution to the effective charge density.

With reference to the nature of processes related to the flow of ions in the fibres (the flow of ions from internal towards external regions and vice versa—for the mechanisms describing the nature of such flow is presented in ref. [4,5] and references therein) we assume a sigmoidal function that is often used to describe the likelihood of the membrane activation and deactivation [6] (and references therein), expressed by the relationship:

$$f(x) = \frac{A}{1+e^{(x/k)}} \qquad (12)$$

To include the above-mentioned charge flow processes, we adapt the function (11) to describe the delayed charge density $\rho_{(t-t0)\pm}$ that we write in the following form:

$$\rho_{(t-t_0)\pm}(x,t) = \frac{\pm a_\pm(x,t)}{1+e^{[(x-x_0)/k_{x\pm}-(t\pm t_0)/k_{t\pm}]}} \qquad (13)$$

The $k_x$ parameters occurring here are related to the velocity of the charge wave travelling along the fibre, while $k_t$ are associated with the rate of the charge density growth during the depolarization process in a given part (W, M, N) of the fibre. The amplitude a(x,t) is defined as follows:

$$a_\pm(x,t) = A_{G\pm}\left(\frac{1}{1+e^{[-(t-t_0)/k_t-]}} - \frac{1}{1+e^{[-(t+t_0)/k_t+]}}\right) \times \left(\frac{1}{1+e^{[-(x-x_0)/k_t-]}} - \frac{1}{1+e^{[-(x+x_0)/k_t+]}}\right) \qquad (14)$$

where the amplitude $A_{G\pm}$ corresponds to the charge density characteristic for a given part (W, M N) of a fibre or, after generalization, a bundle of fibres.

The $t_0$ parameter determines physically the time delay, which—as it was mentioned earlier—leads to a non-vanishing contribution to the total charge density. This contribution originates from the processes that have just started inside the fibre. It should also be remembered that this value is related to the velocity of charge wave propagation along the fibres and hence the $x_0$ parameter occurs in equations (13) and (14). In further calculations, a small volume dv', which is located in a place shifted by certain $x_0$, is considered. The charge within this volume gives a delayed contribution to the calculated potential. In fact, the problem is similar to the determination of the time step in a numerical integration procedure. Then, the changes in the density of positive and negative charges in these regions (1 and 2) can be finally presented in the following form:

$$\rho_\pm(x',t') = A_G\left(\frac{1}{1+e^{[-(t'-\Delta t')/k]}} - \frac{1}{1+e^{[-(t'+\Delta t')/k]}}\right) \cdot \left(\frac{1}{1+e^{[-(x'-\Delta x')/k]}} - \frac{1}{1+e^{[-(x'+\Delta x')/k]}}\right) \cdot \frac{1}{1+e^{[(x'+\Delta x')/k_{x'}-(t'\pm\Delta t')/k_{t'\pm}]}} \pm A\frac{1}{1+e^{[-(t'-\Delta t')/k]}} \cdot \frac{1}{1+e^{[-(x'-\Delta x')/k]}} \qquad (15)$$

Due to a large number of parameters describing this model, they were reduced using appropriate assumptions. The cardiac muscle consists of many bundles of such fibres and therefore their mathematical description in a full form is far beyond our analytical and numerical computing capabilities. Thus, assuming that the time moments associated with the beginning and the end of the depolarization process are related to the beginning and the end of a given part of the fibre, (W, M, N), respectively, we can unify the $k_t$ and $k_x$ parameter values for the intra- (positive charges +) and extracellular (negative charges −) regions. Furthermore, for future considerations, we should assume that the x and t values are limited to certain ranges due to the physical dimensions of the fibre and the properties of the depolarization processes, in particular by the passage time of the stimulation wave. The $t_{0\pm}$ and $x_{0\pm}$ parameters can be determined from the properties, in particular from the conductivity of a given fibre segment. FIG. 5 shows the dependence of the positive ($\rho_+$) and negative ($\rho_-$) electric charge density on the position and time, as calculated with formula (15).

Based on the relationship (11), the effective charge density was also calculated, as shown in FIG. 6.

FIG. 7 shows the density calculated as a function of the position measured along a single fibre for different time moments. We can notice that the total charge density has a characteristic spatial distribution and reaches its maximum values at the time moments located centrally in the time interval that is related to the duration of the process we are interested in. For these time moments $\Delta\rho$ is characterised by a dispersion-like curve.

The time of density evolution shown in FIG. 7 (*a*) features similar but not identical character. As one can notice, the highest density values are reached in the central part of the fibre segment for $x \cong 50\%$. In addition, in this case the curve characterising the total charge density features a dispersive character.

Analysis of Electrocardiograms

The resting electrocardiograms from twelve leads were recorded using a standard ECG apparatus which enabled measurements of potentials in the frequency band corresponding to the AHA standard for analogue filtration (0.03-100 Hz). Potential values for each lead were normalized and averaged according to the criteria described hereinafter. The isoelectric (zero) line was determined on the basis of the T-P section.

The above-described physical foundations of the depolarization process giving rise to emergence of potentials on the surface of the chest indicate that during this process many partial potentials appear, each of them being related to the distribution of the resultant charge density $\Delta\rho_i$ in the individual segments (W, M, N) of a given bundle. Using the procedures described below, the parameters of these potentials are optimized in such a way as to obtain the best possible match of the course of their resultant value with the ECG measurement data. Most of them assume negative and positive values during the depolarization (FIG. 8), indicating the complexity of the QRS complex analysis using the method according to the invention. For the sake of clarity of the drawing, five potentials are marked, each of which is the sum of the partial potentials originating from a given bundle representing different area of the myocardium.

The QRS complex is decomposed into at least five negative/positive potentials or ten individual potentials, each of them being negative or positive, which are treated as the information carriers about the activity of the interventricular septum and the anterior, inferior, lateral, and posterior walls. In this case, we determine five effective fibres representing the charge flows inside the working myocardial fibres of a given area. Each of them consists of three parts (marked by W, M and N). The boundary conditions between them are selected so, thanks to the analytic function described in equation (11), that the density at the boundary equals to zero. This means that the function describing the charge density is continuous (in the mathematical sense) along the entire length of a single effective fibre.

The analysis of electrocardiograms (in particular the QRS complexes) is carried out in accordance with the following procedures:

1. Determination of Centre Points

The positions of the centre points for QRS complexes are calculated for each of the 12 leads by the software provided by the manufacturer of the ECG apparatus. These points are marked with vertical markers in FIG. 9.

2. Determination of the Most Similar QRS Complexes

For each of the leads at least two least different QRS complexes are determined from all the evolutions. This is done by calculating the difference in the absolute value of the potential around the centre point (e.g., ±50 samples) and selecting for averaging the QRS complexes with the smallest difference in potential value, as shown by arrows in FIG. 10.

3. Calculation of Averaged Potentials

From selected QRS complexes (as above), for each lead we calculate averaged waveforms of the QRS complexes, as shown in FIG. 11.

4. Transformation to Orthogonal (X, Y, Z) Frank System

The values of the averaged potentials are transformed into the orthogonal Frank system based on the transformations described in the literature [7] and using the empirically obtained coefficients. Using the known methods [8,9] for determining the electrical axis of the heart, approximate angles in the orthogonal system are calculated, at which the physical heart axes: sagittal, transverse and anatomical, are inclined. Then, the orthogonal system is transformed into a system associated with the anatomical axes of the heart in that the Y axis is brought to its long anatomical axis, while the Z axis is brought to the sagittal axis. In these transformations, matrices used in the three-dimensional right-handed system were used with the following directions of positive rotation [10]:

$$x \to y, y \to z, z \to x \quad (15)$$

In each case, the heart-related coordinate system was so pre-oriented in relation to the orthogonal system that the individual angles had the following values:
around the OX axis: $-15.5°$ (where "+" is from Y→Z)
around the OY axis: $-39.0°$ (where "+" is from X→Z)
around the OZ axis: $-35.0°$ (where "+" is from X→Y)

FIG. 12 shows components of the resultant potentials in the orthogonal (X, Y, Z) coordinate system.

5. Determination of Extreme Values of Partial Potentials

Based on the theoretical SFHAM model, at least ten potentials associated with the distribution of the resultant charge density $\Delta\rho$ appear during the ventricular depolarization along five bundles representing individual areas of the myocardium. The source of the emerging potential is the movement of the resultant electric charge along the bundle. A similar issue was analyzed by Clayton et al. [11] who considered the course of the potential along a one-component fibre. The value of each potential appearing on the surface of the chest at a given time $t_0$ depends on physiological and pathological factors. The influence of physiological factors on the potential value was analyzed in the further part of the study taking into account various parameters related to the structure and location of the heart. The individual anatomical areas of the myocardium are represented by characteristic bundles, therefore in order to uniquely determine their spatial orientation an orthogonal coordinate system was used—FIG. 13 (c). The (α,β) angles determine the bundle position in a system associated directly with the patient, indicating at the same time the propagation direction of the depolarization wave from the endocardium W to the epicardium N. The distance between the centre of the bundle and the $(XY)_n$ plane tangent to the anterior surface of the chest is marked by $r_0$.

The potential at a given point of the $(XY)_n$ plane under consideration depends, inter alia, on the distance $r_0$, the angles (α,β) and the amplitude of the resulting charge density ($A_1$), which arises in every part of the active bundle ($A_w$, $A_m$, $A_n$). Assuming α=0° and $A_1$=const., the potential values (φ) along the x axis for three different distances $r_0$=20; 30; 40 were calculated. These dependencies are shown in FIGS. 13 (a) and 13 (b) for β=0° and β=−31°, respectively. For β=0°, an asymmetric waveform of the potential with the maximum on the endocardium side and minimum on the epicardium side is observed for each of the three $r_0$ distances. With increasing $r_0$ distance, the absolute value of the potential decreases, and the maximum and minimum move away from the centre of the bundle, with the maximum potential being closer to the centre and always on the endocardium side.

Rotation of the bundle in the YZ plane by β=−31°, while keeping the remaining parameters unchanged, gives different potential distribution φ(x), as shown in FIG. 13 (b). Then, the absolute potential value, e.g., for $r_0$=20, is about three times greater than in the previous case, wherein the potential distribution along the x axis at a distance $r_0$=40 for rotation angles β=−57° and β=+57° has a completely different character and runs as shown in FIG. 14 (a). In this case, only one (positive or negative) potential extremum is clearly seen. In fact, the individual CM bundles are inclined at different angles and are located at different distances from the measurement point, contributing independently to the resultant potential φ. Moreover, each of the CM bundles has its own characteristic number of fibres, which was included in the calculations by taking the appropriate amplitude value $A_1$ associated with the resultant charge density.

FIG. 14 (b) shows the potential distribution φ(x) for three bundles with different amplitude values A. The presented calculations show that the amplitude value does not affect the position of the extreme potential values with respect to the centre of the bundle. Thus, the spatial potential distribution does not depend on the size of the heart, as long as the (β) angle and the $r_0$ distance are the same in both cases.

Based on the model indicated here, time dependencies for each of the instantaneous potentials at a given point in space were also analyzed. In recent years, much attention has been paid to the differences in shape and duration times of functional potentials originating from working fibres in individual parts of the myocardium [12,13,14]. The results of these studies indicate that the stimulation of the cells in the subendocardial part (W) and the M cells starts almost simultaneously, which is probably related to the penetration of a certain amount of the Purkinje fibres deeply under the endocardium [15]. In turn, the stimulation of the cells in the subepicardial part occurs slightly later. The duration of the potential of the stimulated M cells is much longer than in other parts, because they account for about 40% of the entire bundle length [16]. Taking into account the above-mentioned temporal relationships, FIG. 15 (a) shows a temporal relationship of the resultant potential φ(t) calculated at a given point in space P(x, y, z) for one of the CM bundles, which is represented by the function marked with thicker solid line (-). The potential φ(t) is essentially influenced by the properties of the individual W, M and N parts, marked with curves (---, -, •••), respectively. The time $t_0$ at which the potential reaches its maximum value is marked with vertical line. The area (P) under the φ(t) curve as shown in FIG. 15 (a) was calculated and treated as 100% in further analyses. FIGS. 15 (b), 15 (c) and 15 (d) show the effect the individual parts of the bundle (W, M, N) have on the P value, time $t_0$ and the nature of the φ(t) waveform. For example, disregarding the potential originating from the subepicardial part (W) of a given CM area (FIG. 15 (b)) results in reduction of the P surface by about 40%, and the time to obtain the maximum potential value is increased by about $2 \times 10^{-3}$ s.

If, on the other hand, the M cells are not involved during the depolarization (FIG. 15 (c)), then the P value decreases by approximately 34% and the time $t_0$ remains unchanged. Depending on the contributions of particular parts of the bundle to the depolarization process, we observe different values of instantaneous potentials and times for which the potential achieves the maximum value. Based on the model presented here, it is also possible to analyze various combinations of contributions from particular parts, including the changes in the amplitude (FIG. 16 (a)) and the velocity of charge movement in both considered areas (I and II) for each part of the bundle. If there is a difference in the ion outflow rates for areas I and II, the φ(t) dependence may also have a negative/positive course as shown in FIG. 16 (b).

Based on the model presented here, the potential waveforms have negative or positive values depending on the bungle angle in the XYZ coordinate system. A detailed analysis of the partial potentials with the program according to the invention takes into account all the aforementioned cases which may occur simultaneously with various intensities, as shown in FIG. 17.

In spite of the fact that in the model discussed here the bundle is made of fibres stimulated at the same time, each of them contributes its own independent contribution to the overall image of the bundle's action and thus the relevant area of the myocardium. Individual CM bundles are activated at different times and in a strictly defined order they contribute to the potential generated around the heart. On the other hand, different parameters for each bundle and their mutual arrangement in space (connected with the heart's structure) result also in anisotropic changes of the physical quantities on the chest.

One should also mention the influence of the dielectric properties of the human body on the measured electric potential. Due to the fact that the model operates with arbitrary values and units, and the fact that for real values of the measured parameters the dielectric characteristics of such medium as the human body can be treated as a linear one, the above equations are sufficient for our purposes. It should be kept in mind, however, that although these relations are not complex in their form, due to the actual form of the functions describing the densities of positive and negative charges and the geometry of the system, finding an exact analytical expression determining the potential value in a compact form is virtually impossible, in spite of the assumptions on one-dimensional character of the single fibre model. This is related to the forms of integrals that determine the potential values as a function of charge density for the fibres under consideration. In addition, the total potential that is reflected in the measured ECG is equal to the sum of potentials originating from the resultant charge in individual fibres. Consequently, we would have to find a compact analytical solution for the expression which takes into account the integration limits determined by the positions of the beginning and the end of each fibre, and to sum up over all the fibres in the area of interest, which represent a difficult calculation. In addition, for each fibre we would have to find the proper integral, remembering that for each of them a different integration limit should be taken—each fibre has a somewhat different geometry and slightly different start time of these processes. The potential values can be, however, calculated numerically, and consequently, the parameters of interest can be calculated with a satisfying accuracy.

Most of the biomedical signals, including those obtained from the ECG tests, are non-stationary, therefore the assessment of their waveforms along with the determination of the initial parameters of each of the partial potentials was made for the time-frequency signal representation. The analysis was transferred to that domain by means of a numerical operation, in which algorithms enabling the change of the resolution of this representation were additionally applied. A similar way of signal processing was described in detail by the authors of ref. [17,18,19,20]. For example, for each averaged XYZ component for one of the patients (ID 17081714.K08), the QRS complex was decomposed, as shown in FIG. 18, as a result of the use of deconvolution and convolution, as well as of signal filtration using a non-recursive low-pass filter.

6. Determination of Optimal Rotation Angles

The correct calculation of the partial potential parameters based on the measured electrocardiograms depends mainly on the determination of the extreme positions of their values. This is accomplished through a series of transformations of the components of the resultant potential in the orthogonal (XYZ) coordinate system that make use of the matrices used in the three-dimensional right-handed system (as described earlier).

This is done by determining the twist angle of the heart's axis and rotating the coordinates in the range 0-90 degrees with respect to the two selected axes by $(\alpha,\beta)$ angles to obtain the best decomposition of the QRS complex. Each time, having done the rotation, the positions of the extrema are determined for each of the partial potentials and for individual (XYZ) coordinates, and the sum between the corresponding extrema is calculated for individual (XYZ) coordinates. The algorithm determines the angles for which the calculated value is at its minimum, i.e., the differences in positions of the respective extrema are the smallest. The positions of the extrema are determined by time or by the sample corresponding to the time. For example, for the first potential the extremum along the X axis is in the 50th sample, along the Y axis in the 55th sample, and along the Z axis in the 45th sample. By making rotation, the algorithm determines the angles for which differences in the positions of the extrema are the smallest for each of the potentials in the XYZ system, respectively. An example is shown in FIG. 19.

Taking into account the earlier assumptions of the model and the function describing the spatial and temporal dependence of the emerging potential, we can also calculate the waveforms of the negative and positive potential values for individual parts of the fibres without rotation, as shown in FIG. 20. The results are plotted in the Frank lead system together with the origin of the coordinate system located in the centre of the heart, the x-axis directed towards the patient's left hand, the y axis in the direction of his feet, while the z-axis points to the patient's back. The sum of the theoretically calculated partial potentials agrees very well with the potential values obtained from the ECG measurements. Similarly, FIG. 21 shows the potential waveforms for optimally selected rotation angles.

For example, FIG. 22 shows two potential waveforms occurring during the depolarization of the anterior wall (SP) along the Y axis together with marked parameters ($S_{\dot{S}P(1)}$, $S_{\dot{S}P(2)}$, $t_{0;\dot{S}P(1)}$, $t_{0;\dot{S}P(2)}$ and $t_{k;\dot{S}P(1)}$ and $t_{k;\dot{S}P(2)}$), which are important for the assessment of the activity of this CM area.

The results can also be presented in the form of negative/positive partial potentials for each stimulation (PR, ŚP, ŚD, ŚB and ŚT), as shown in the Frank lead system in FIG. 23.

7. Calculation of Parameters Describing Partial Potentials a). The potential appearing during the stimulation of each bundle is described first using partial potentials, which are marked in the order of appearance 1 or 2, respectively, in FIG. 21 and FIG. 22. The electrical activity of individual areas is evaluated based on the calculated values of parameters $A_{1,i}$ and $A_{2,i}$, where i=(PR, ŚP, ŚD, ŚB, ŚT), for the interventricular septum, and the anterior, inferior, lateral, and posterior walls. The parameters for the first potential are calculated in the time interval $(t_{0(1)} \to t_{k(1)})$ for each component of the orthogonal (X Y Z) coordinate system, with the formula:

$$A_{1,i} = \sum_{j=\{x,y,z\}} \int_{t_{0(1),i}}^{t_{k(1),i}} |V_{1,i,j}| dt; \text{ where } i = \{PR, \acute{S}P, \acute{S}D, \acute{S}B, \acute{S}T\} \quad (16)$$

Similarly, the $A_{2,i}$ parameter for the second potential is defined and calculated in the time interval $(t_{0(2)} \to t_{k(2)})$ $$A_{2,i} = \sum_{j=\{x,y,z\}} \int_{t_{0(2),i}}^{t_{k(2),i}} |V_{2,i,j}| dt; \text{ where } i = \{PR, \acute{S}P, \acute{S}D, \acute{S}B, \acute{S}T\} \quad (17)$$

as well as the parameter describing the resultant activity ($A_{wyp}$) in the time interval $(t_0 \to t_{end})$.

$$A_{wyp} = \Sigma_{j=\{x,y,z\}} \int_{t_0}^{t_{end}} |V_{wyp,j}| dt \quad (18)$$

where $V_{wyp}$ is the measured potential.

Similarly, we define and calculate parameters for normal potentials, which are treated as parameters of the norm, ($N_{1,i}$, $N_{2,i}$ oraz $N_{wyp}$), respectively.

In order to refer to the activity parameters defined above to the norm and the resultant activity of a given area, normalized potentials ($U_{1,i}$; $U_{2,i}$ oraz $U_{wyp}$) are defined as follows:

$$U_{1,i} = \frac{A_{1,i} N_{wyp}}{N_{1,i} A_{wyp}} \cdot 100\%; \text{ where } i = \{PR, \acute{S}P, \acute{S}D, \acute{S}B, \acute{S}T\}, \quad (19)$$

$$U_{2,i} = \frac{A_{2,i} N_{wyp}}{N_{2,i} A_{wyp}} \cdot 100\%; \text{ where } i = \{PR, \acute{S}P, \acute{S}D, \acute{S}B, \acute{S}T\}, \quad (20)$$

$$U_{wyp} = \frac{A_{wyp}}{N_{wyp}} \cdot 100\% \quad (21)$$

In order to assess the change in the electric charge distribution in particular areas of the myocardium, the factor (J) is calculated with the formula:

$$J_i = \frac{U_{2,i}}{U_{1,i}}; \text{ where } i = \{PR, \acute{S}P, \acute{S}D, \acute{S}B, \acute{S}T\}. \tag{22}$$

The duration times of the partial potentials are described by the dependencies:

$$t_{1,i} = \sum_{j=\{x,y,z\}} \left((t_{k(1)} - t_{0(1)})_j\right)_i; \text{ where} \tag{23}$$

$$i = \{PR, \acute{S}P, \acute{S}D, \acute{S}B, \acute{S}T\}$$

$$t_{2,i} = \sum_{j=\{x,y,z\}} \left((t_{k(2)} - t_{0(2)})_j\right)_i; \text{ where} \tag{24}$$

$$i = \{PR, \acute{S}P, \acute{S}D, \acute{S}B, \acute{S}T\}$$

These parameters are also referred to the norm and calculated with the following formulae:

$$t_{1,i}^{cz} = \frac{t_{1,i}}{t_{N_{1,i}}} \cdot 100\%; \text{ where } i = \{PR, \acute{S}P, \acute{S}D, \acute{S}B, \acute{S}T\} \tag{25}$$

$$t_{2,i}^{cz} = \frac{t_{2,i}}{t_{N_{2,i}}} \cdot 100\%; \text{ where } i = \{PR, \acute{S}P, \acute{S}D, \acute{S}B, \acute{S}T\} \tag{26}$$

The calculated parameters are expressed in % and for perfectly running depolarization processes should amount to 100%. The values of the calculated parameters give the opportunity to assess the potential appearing on the surface of the chest during the depolarization of the areas of the left ventricular muscle (CM).

b). The results of the analysis can also be presented in the form of negative/positive partial potentials that are the sum of single (negative or positive) potentials for each of the five areas: the interventricular septum (PR), and the anterior (ŚP), inferior (ŚD), lateral (ŚB), and posterior walls.

Then, it is also possible to analyze the partial potential of each of the CM areas under consideration. For example, FIG. 23 shows the course of the potential appearing during the depolarization of the inferior wall, which is the sum of the single potentials 1 and 2 (in this case with a negative and positive values).

The electrical activity of individual CM areas during the depolarization can be assessed using the parameter values, i.a., $A_i^{(1)}$, where i=(PR, ŚP, ŚD, ŚB, ŚT), for the interventricular septum and the anterior, inferior, lateral, and posterior walls, respectively. The parameter is calculated in the time interval ($t_0 \to t_1$) for each component of the orthogonal (x y z) coordinate system.

$$A_i^{(1)} = \sum_{j=\{x,y,z\}} \int_{t_0}^{t_1} |V_{i,j}^{(1)}| dt; \text{ where } i = \{PR, \acute{S}P, \acute{S}D, \acute{S}B, \acute{S}T\} \tag{27}$$

Similarly, the $A_i^{(2)}$ parameter is defined and calculated for the positive potential values in the interval ($t_1 \to t_2$):

$$A_i^{(2)} = \sum_{j=\{x,y,z\}} \int_{t_1}^{t_2} |V_{i,j}^{(2)}| dt; \text{ where } i = \{PR, \acute{S}P, \acute{S}D, \acute{S}B, \acute{S}T\} \tag{28}$$

as well as the parameter describing the resultant activity ($A_{wyp}$) in the interval ($t_0 \to t_{end}$).

$$A_{wyp} = \sum_{j=\{x,y,z\}} \int_{t_0}^{t_{end}} |V_{wyp,j}| dt \tag{29}$$

where $V_{wyp}$ is the measured potential.

As in the previous case, we calculate the parameters for the non-perturbed electrical activity treated as a norm, ($N_i^{(1)}$, $N_i^{(2)}$ and $N_{wyp}$), respectively. In order to refer to the activity parameters defined above to the norm and the resultant activity of a given segment, normalized potentials $V_{cz,i}^{(1)}$, $V_{cz,i}^{(2)}$ oraz $V_{wyp}$) are defined as follows:

$$V_{cz,i}^{(1)} = \frac{A_i^{(1)} N_{wyp}}{N_i^{(1)} A_{wyp}} \cdot 100\%; \text{ where } i = \{PR, \acute{S}P, \acute{S}D, \acute{S}B, \acute{S}T\}, \tag{30}$$

$$V_{cz,i}^{(2)} = \frac{A_i^{(2)} N_{tot}}{N_i^{(2)} A_{tot}} \cdot 100\%; \text{ where } i = \{PR, \acute{S}P, \acute{S}D, \acute{S}B, \acute{S}T\} \tag{31}$$

$$V_{wyp} = \frac{A_{wyp}}{N_{wyp}} \cdot 100\% \tag{32}$$

In this case, we can also assess the changes in the electric charge distribution during the depolarization in each of the areas of the left ventricular muscle under consideration. To this end, we introduce a coefficient (JJ) defined by the relationship:

$$JJ_i = \frac{V_{cz,i}^{(2)}}{V_{cz,i}^{(1)}}; \text{ where } i = \{PR, \acute{S}P, \acute{S}D, \acute{S}B, \acute{S}T\}, \tag{33}$$

The duration times of the individual potentials are described by the dependencies:

$$t_i^{(1)} = \sum_{j=\{x,y,z\}} \left((t_1^{(1)} - t_0^{(1)})_j\right)_i; \text{ where} \tag{34}$$

$$i = \{PR, \acute{S}P, \acute{S}D, \acute{S}B, \acute{S}T\}$$

$$t_i^{(2)} = \sum_{j=\{x,y,z\}} \left((t_2^{(2)} - t_1^{(2)})_j\right)_i; \text{ where} \tag{35}$$

$$i = \{PR, \acute{S}P, \acute{S}D, \acute{S}B, \acute{S}T\}$$

These parameters are also referred to the norm and calculated with the following formulae:

$$t_{cz,i}^1 = \frac{t_i^{(1)}}{t_{N_i}^{(1)}} \cdot 100\%; \text{ where } i = \{PR, \acute{S}P, \acute{S}D, \acute{S}B, \acute{S}T\} \tag{36}$$

$$t_{cz,i}^2 = \frac{t_i^{(2)}}{t_{N_i}^{(2)}} \cdot 100\%; \text{ where } i = \{PR, \acute{S}P, \acute{S}D, \acute{S}B, \acute{S}T\} \tag{37}$$

The calculated parameters are expressed in % and for perfectly running depolarization processes should amount to 100%.

The assessment of the above-calculated parameters of the negative/positive partial potentials gives the opportunity to assess the potential appearing on the surface of the chest during the depolarization of individual areas of the left ventricular muscle (CM).

REFERENCES

[1] Janicki J. S., Leoński W., Jagielski J., "*Partial potentials of selected cardiac muscle regions and heart activity model based on single fibres*", Medical Engineering & Physics, 31 (2009) 1276-1282.

[2] Franz M. R., Bargheer K. et al., "*Monophasic action potential mapping in human subjects with normal electrocardiogram: direct evidence for the genesis of T wave.*", Circulation, 75 (1987) 379.

[3] Litovsky S. H., Antzelevitch C., "*Rate dependence of action potential duration and refractoriness in ventricular endocardium differs from that of epicardium: role of the transient outward current.*", J. Am. Coll. Cardiol., 14 (1989) 1053.

[4] Malmivuo J., Plonsey R., "*Bioelectromagnetism*", New York and Oxford, Oxford University Press, 1995.

[5] Bers D. M. "*Excitation-contraction coupling and cardiac contractile force*", 2nd ed., Dordrecht-Boston-London, Kulwier Academic Publishers, 2001.

[6] Rubart M., Zipes D., "*Heart disease: a textbook of cardiovascular medicine*" chapter in: "*Genesis of cardiac arrythmias: electrophysiological considerations*", Philadelphia, W. B. Saunders Co., 2001.

[7] Levkov L. C. "*Orthogonal electrocardiogram derived from the limb and chest electrodes of the conventional 12-lead system*", Med. Biol. Eng. Comput. 25 (1987) 155.

[8] Dąbrowska B., Dąbrowski A. "*Handbook of electrocardiography*", for medical students and professionals, in Polish, original title "*Podręcznik elektrokardiografii,*" 1999, 4th edition.

[9] Węsław T., "*Normogram for determination of the electric axis of the cardiac muscle*", in Polish, original title "*Normogram do określania osi elektrycznej serca,*" Kardiologia Polska, Kardiol. Pol., 6 (1963) 113.

[10] Le Grice I. J., Hunter P. J., Smaill B. H., "*Laminar structure of the heart: A mathematical model,*" Am. J. Physiol., 272 (1997) H2466-H2476.

[11] Clayton R. H., Parkinson K., Holden A. V., "*Re-entry in computational models of ischaemic myocardium*", Chaos, Solitons and Fractals, 13 (2002) 1671-1683.

[12] Franz M. R., Bargheer K. et al., "*Monophasic action potential mapping in human subjects with normal electrocardiogram: direct evidence for the genesis of T wave.*", Circulation, 75 (1987) 379.

[13] Litovsky S. H., Antzelevitch C., "*Rate dependence of action potential duration and refractoriness in ventricular endocardium differs from that of epicardium: role of the transient outward current.*", J. Am. Coll. Cardiol., 14 (1989) 1053.

[14] Drouin E, Charprentier E F. et al., "*Electrophysiologic characteristics of cells spanning the left ventricular wall of human: evidence for presence of M cells,*" J. Amer. Coll. Cardiol., 26 (1995) 185.

[15] Litovsky S. H., Antzelevitch C., "*A subpopulation of cells with unique electrophysiological properties in the deep subendocardium of the canine ventricle. The M cell*", Circ. Res., 68 (1991) 1729.

[16] Antzelevitch C., Sicouri S., Lucas A. et al., "*Regional differences in the electrophysiology of ventricular cells: physiological and clinical implications*" in "*Cardiac electrophysiology: from cell to bedside*", Eds. Zipes D. P., Jalife J., Saunders W. B., Comp., Philadelphia, 1995, p. 228.

[17] Daubechies I., "*The wavelet transform, time-frequency localizations and signal analysis*" IEEE Transaction on Inform. Theory, 35(5) (1990) 961-1005.

[18] Sahambi J. S., Tandon S. N., Blatt R. K. P., "*Using wavelet transform for ECG characterization*", IEEE EMB Magazine, January/February 1997, pp. 77-83.

[19] Hormac C., Vetterli M., "*Orthogonal time-varying filter banks and wavelet packets*", IEEE Transaction on Signal Processing, 10(42) (1994) 2650-2663.

[20] Vetterli M., "*Wavelets and filter banks*" IEEE Transaction on Signal Processing, 9(40) (1992) 2207-2232.

[21] Janicki J S, Teresińska A, Leoński W, Chąpiński M, Sobieszczańska M, Piotrowicz R, "*Application of SFHAM Model for Diagnosis of Ischemic Heart Disease 1*", Electrocardiology 2014—proceedings of the 41st International Congress on Electrocardiology, 7 Jun. 2014 (2014 Jun. 7, pages 187-190

The invention claimed is:

1. A method for decomposing a resultant electric potential (Vwyp) forming a QRS complex in an electrocardiogram (ECG) into partial potentials corresponding to depolarization of specific areas (/) of a left ventricular muscle (MS), in which decomposition is carried out in such a way that on the basis of a theoretical SFHAM (single fiber based heart activity model) of electrical heart activity, mathematical functions describing changes in the partial potential values are determined, and then their parameters are selected so that superposition of the values of these functions is as close as possible to a resultant potential (Vwyp) measured during an ECG test, wherein each of the partial potentials is described by two functions: V1,i (t) and V2,i (t), corresponding to the depolarization of a specific area of the left ventricular muscle, each of these functions has negative or positive values and one extremum, wherein a beginning of an emergence of these potentials (t0(1),i and t0(2),i) and their end (tk(1),i and tk(2),i) is considered the time at which the potential value is greater than its arbitrarily set minimum value, and a sum of the values of these potentials determines the electrical activity of the specific area of the left ventricular muscle, the method comprising:

obtaining, from the ECG test, a signal indicative of the electrical heart activity;

obtaining, from the signal, a plurality of electric potential values corresponding to measurements of the electrical heart activity, wherein the plurality of electric potential values includes the partial potential values;

calculating, using the plurality of electrical potential values obtained from the signal, an order of occurrence of extrema of the partial potential values, wherein the order of occurrence of the extrema is determined from the theoretical SFHAM model of electrical heart activity, and positions of the extrema are determined by, using a computer:

making a series of transformations of the partial potential values for (X Y Z) coordinates in the orthogonal system, comprising rotation of the coordinates in the range (0÷90°) with respect to two selected axes by (α, β) angles, calculating, for each rotation angle, the positions of extrema of the partial potentials for each of the (XYZ) coordinates, by using deconvolution and convolution, and a low-pass filter with parameters corresponding to the function describing the partial potentials, and then selecting the angles for which the differences in the positions of extrema for each of the partial potentials in the XYZ system, respectively, are the smallest; and outputting, using the order of occurrence of the extrema, an analysis of results of the ECG test.

2. The method according to claim 1, wherein each partial potential corresponds to an interventricular septum (PR), anterior wall (SP), inferior wall (SD), lateral wall (ŚB), and posterior wall (ŚT), respectively.

3. The method according to claim 1, an analysis of resultant potentials (QRS complexes) is made on the basis of averaged values for each lead, transformed into the orthogonal Frank system.

4. A method of determining a parameter describing resultant electrical activity of the left ventricular muscle (CM), wherein, having determined parameters of the functions V1,i (t) and V2,i (t), describing the waveforms of the partial potentials by means of the method according to claim 1, an area under a curve of each of the partial potentials for X, Y, Z coordinates is calculated in accordance with:

$$A_{1,i} = \sum_{j=\{x,y,z\}} \int_{t_{0(1),i}}^{t_{k(1),i}} |V_{1,i,j}| dt$$

$$A_{2,i} = \sum_{j=\{x,y,z\}} \int_{t_{0(2),i}}^{t_{k(2),i}} |V_{2,i,j}| dt$$

where t0(1),i and t0(2),i denote respective times the partial potentials begin to appear, and tk(1),i and tk(2),i denote respective times the partial potentials stop appearing, and subsequently a parameter describing resultant electrical activity of ventricles is calculated in accordance with:

$$A_{wyp} = \sum_{j=\{x,y,z\}} \int_{t_0}^{t_{end}} |V_{wyp}| dt.$$

5. A method of determining a parameter describing resultant electrical activity of the left ventricular muscle (CM), wherein, having determined the parameters of the functions V1,i (t) and V2,i (t), describing the waveforms of the partial potentials by means of the method according to claim 1, an area under a curve of each of the partial potentials for X, Y, Z coordinates is calculated in accordance with:

$$A_{1,i} = \sum_{j=\{x,y,z\}} \int_{t_{0(1),i}}^{t_{k(1),i}} |V_{1,i,j}| dt$$

$$A_{2,i} = \sum_{j=\{x,y,z\}} \int_{t_{0(2),i}}^{t_{k(2),i}} |V_{2,i,j}| dt$$

where t0(1),i and t0(2),i denote respective times the partial potentials begin to appear, and tk(1),i and tk(2),i denote respective times the partial potentials stop appearing, and subsequently normalised partial potentials (U1,i, U2,i and Uwyp) are calculated in accordance with:

$$U_{1,i} = \frac{A_{1,i} N_{wyp}}{N_{1,i} A_{wyp}} \cdot 100\%;$$

$$U_{2,i} = \frac{A_{2,i} N_{wyp}}{N_{2,i} A_{wyp}} \cdot 100\%;$$

$$U_{wyp} = \frac{A_{wyp}}{N_{wyp}} \cdot 100\%;$$

wherein (N1,i, N2,i oraz Nwyp) are parameters determined for the partial potentials with normal electrical activity treated as a norm;

and further a parameter describing a change in electric charge distribution during depolarization of each myocardium area is calculated in accordance with:

$$J_i = \frac{U_{2,i}}{U_{1,i}}.$$

6. A device configured to implement the method according to claim 1.

\* \* \* \* \*